United States Patent [19]

DellaVecchia et al.

[11] Patent Number: 4,850,376

[45] Date of Patent: Jul. 25, 1989

[54] OPHTHALMIC SHIELD WITH REMOVABLE COMPRESSION DEVICE

[76] Inventors: Michael DellaVecchia, 6131 Grays Ave., Philadelphia, Pa. 19142; Richard Naids, 1719 A Rachael St., Philadelphia, Pa. 19115

[21] Appl. No.: 168,785

[22] Filed: Mar. 16, 1988

[51] Int. Cl.[4] .......................... A61F 13/00; A61F 9/00
[52] U.S. Cl. .......................................... 128/858; 2/15
[58] Field of Search ................ 128/132 R, 153, 155, 128/156, 858; 2/15, 433

[56] References Cited

U.S. PATENT DOCUMENTS

| | | | |
|---|---|---|---|
| 1,161,321 | 11/1915 | Lush | 2/15 |
| 2,389,032 | 11/1945 | Donnelly | 128/153 |
| 2,389,223 | 11/1945 | Werner | 2/15 |
| 2,671,898 | 3/1954 | Wade | 128/132 R |
| 3,092,103 | 6/1963 | Mower | 2/15 |
| 3,244,171 | 4/1966 | Neu | 128/153 |
| 4,473,370 | 9/1984 | Weiss | 128/155 |
| 4,581,877 | 4/1986 | Wilber | 128/132 R |

*Primary Examiner*—Robert A. Hafer
*Assistant Examiner*—Michael Brown
*Attorney, Agent, or Firm*—Caesar, Rivise, Bernstein, Cohen & Pokotilow, Ltd.

[57] ABSTRACT

An ophthalmic shield with compression device wherein the ophthalmic shield has at least one enlarged opening and wherein the ophthalmic shield is adapted to be positioned on the head of the wearer in covering relationship to an eye of the wearer. A pad is positioned in the enlarged opening with the pad receiving fluid that drains from the eye.

9 Claims, 2 Drawing Sheets

OPHTHALMIC SHIELD WITH REMOVABLE COMPRESSION DEVICE

FIELD OF THE INVENTION

This invention relates generally to ophthalmic shields, and more particularly, to an ophthalmic shield which in the preferred embodiment includes a compression device which is held to the ophthalmic shield without any special attachment means, such as an adhesive.

Ophthalmic shields are known generally in the practice of ophthalmology. Such shields are typically used in connection with the aftermath of surgical procedures, injury or disease as protective devices to prevent unwanted contact with an eye which has just been the subject of a surgical procedure, injury or disease.

In the normal practice, the ophthalmic shield is taped to the head of a person, using various tacky adhesive tapes. At times, such taping exerts undue adhesion pressure against the head of a patient which adds an element of discomfort to a person whose has been recently subjected to surgery, injury or disease. Also, the removal of such tapes can cause further discomfort and/or dermal pathology especially if sensitized.

BACKGROUND ART

Various shields of protective covers for the eye have been suggested as exemplified by the devices as shown in U.S. Pat. Nos. 2,896,615, 3,446,209, 4,193,401 and Re. 20,873. Also, in U.S. Pat. No. 3,300,786, there is shown an ophthalmic shield having a central opening, but such shield is secured to the head of the wearer by means of tape.

U.S. Pat. No. 4,677,974 shows an eyelid splint which consists of a rigid backing member having an elliptically shaped foam pad mounted on the interior face therof. A pair of straps is provided that are secured at one end to the backing member with the other ends being fastened together by patches of interengaging fastening means.

OBJECTS AND BRIEF DESCRIPTION OF THE INVENTION

It is an object of the present invention to provide an ophthalmic shield which may be simply and quickly secured to or detached from the head of a wearer.

Yet another object of the present invention is to provide an ophthalmic shield which is capable of use in connection with either the right or the left eye of a wearer.

Still another object of the present invention is to possibly provide an ophthalmic shield which readily accepts a replacable compression sterile device, preferably without the use of an adhesive or other securing means.

Still another object of the present invention is to provide an ophthalmic shield which is relatively low in cost.

The foregoing, as well as other objects of the invention are achieved by providing an ophthalmic shield with a compression device wherein the ophthalmic shield has at least one enlarged opening. The ophthalmic shield is adapted to be positioned on and held to the head of a wearer in covering relationship to an eye of the wearer. A pad is positioned in the enlarged opening and is held in such enlarged opening by virtue of the pad being partially stuffed or inserted in and through the opening so that it projects through the opening and outwardly of the opposing face of the shield. This pad will receive fluid that drains from the eye.

The ophthalmic shield also includes an extension which extends to one side. Straps are secured to the ophthalmic shield in a snap fit. The straps comprise two pieces, a first end of which is secured to the ophthalmic shield. Second ends of the straps are adjustably secured together.

The small openings in the opthalmic shield receive in a snap fit enlarged bead projections which extend from first ends of the strap pieces.

Finally, the ophthalmic shield has two first small openings adjacent the extension tab and a second small opening remote from the table extension. These are the openings which receive in the snap fit the enlarged bead portions from the first ends of the strap pieces.

DETAILED DESCRIPTION OF THE INVENTION

Figure 1:
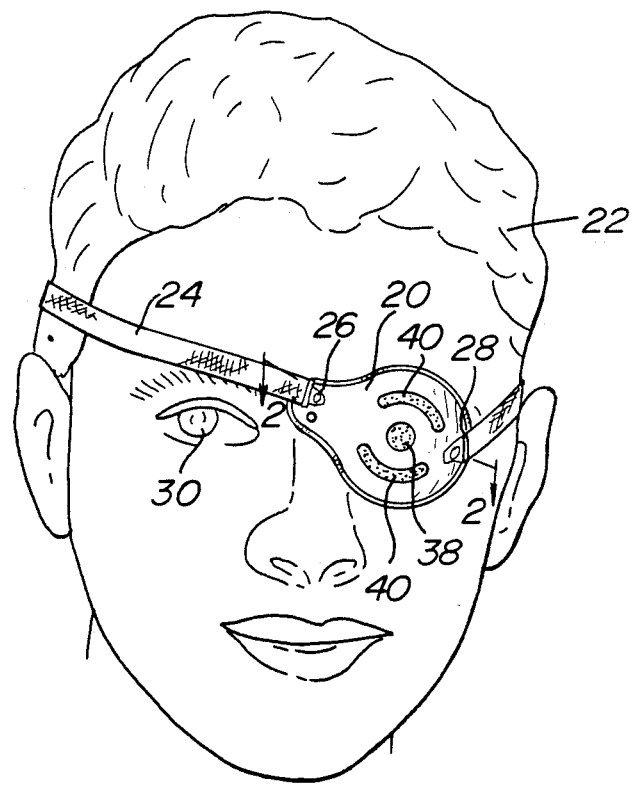
FIG. 1 is a view showing the ophthalmic shield of the present invention secured to the head of a wearer and with a portion of the pad extending through the central opening in the ophthalmic shield.

Referring now to the various figures of the drawings, wherein the like reference character refer to like parts, there is shown at 20 in FIG. 1 an ophthalmic shield of elliptical shape with compression device embodying the present invention wherein the shield 20 is positioned upon the head 22 of a person. The ophthalmic shield 20 is held in operative position to the head of the person through the use of a tapeless, but adjustable one or two-piece strap 24 having first ends 26 and 28 which are secured to the shield 20 at appropriate places, as shown in FIG. 1 and as will be discussed hereinafter.

Figure 2:
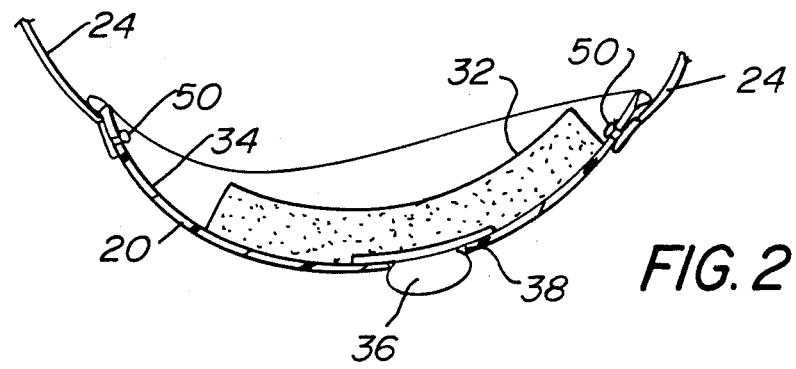
FIG. 2 is an enlarged sectional view taken along the lines 2—2 of FIG. 1.

As shown in FIG. 2, the two-piece strap 24 and encircles the head 22 of the wearer and holds the shield 20 tightly against the head of the wearer in a protective position covering the left eye of the wearer. The other or right eye 30 of the wearer remains unaffected.

A pad 32 (FIG. 2) is positioned against the inner face 34 of the ophthalmic shield 20. The pad 32 is preferably not adhesively or otherwise secured against the inner face 34 of the shield 20. Instead, the pad 32 is sufficiently large to be stuffed in opening held in place by simply having a small portion 36 of the pad 32 pressed through an opening 38 in the shield 20.

As further shown in FIG. 1, the shield 20 possesses not only central opening 38, but also arcuate satellite openings 40 which function to allow for additional viewing and additional light to reach the shield and eye of the patient, once the compression device 32 has been removed.

The shield 20 is basically ellipitical or circular in shape, except for a sidewardly extending tab 42. First, small openings 44 and 46 are formed in the tab 42 which have a strap receiving function. Second, opening 48 is formed in the shield 20 remote from small upper and lower openings 44 and 46, with opening 48 being of the same general size as the small openings 44 and 46.

Figure 4:
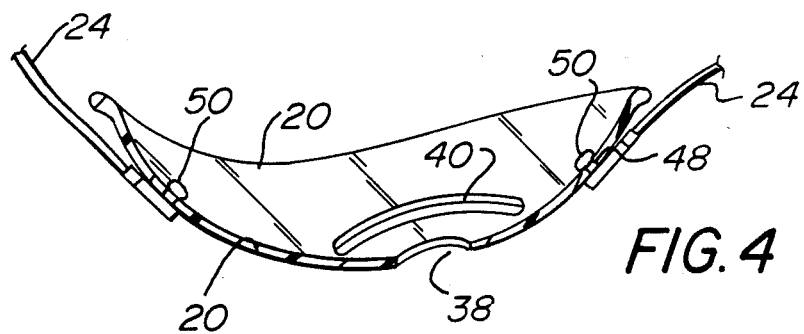
FIGS. 4 and 5 are enlarged sectional views taken along the lines 4—4 and 5—4 respectively of FIGS. 4 and 5.
Figure 5:
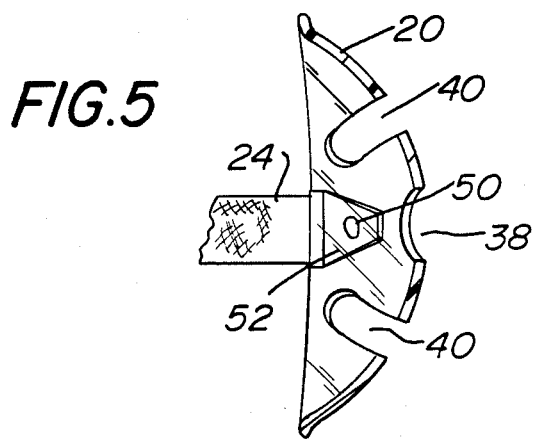

The purpose of the openings 44, 46 and 48 is to receive in a snap fit a slightly enlarged bead 50 (FIGS. 4 and 5), which projects from special end portions 52 which extend from the first ends 26 and 28 of the strap 24. These extensions may be made of a plastic, such as a vinyl plastic, with the special ends 52 and the enlarged beads 50 being molded as a single piece. The special ends 52 may be press fit to each of the ends 26 and 28, respectively of the strap 24.

Figure 3:
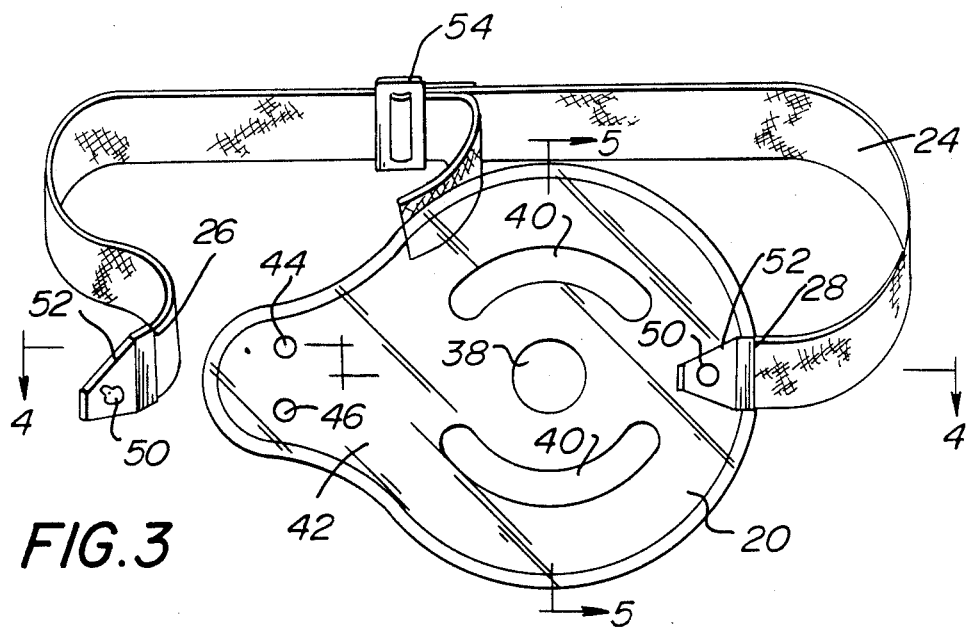
FIG. 3 is a view similar to FIG. 2, but taken from the front of the ophthalmic shield.

As shown in FIGS. 1 and 3, the shield 20 is tightened about the head of a wearer through the use of a buckle 54 (FIG. 3) which receives the remote or second ends 51 and 53 of strap 24. As shown in FIG. 3, an end 51 and 53 of each portion of the strap 24 is received in the buckle 54 which can be slid back and forth in order to accommodate the particular head size of a wearer. In the preferred embodiment, one or both of the two-pieces comprising strap 24 will be of a somewhat elastic material, such that there will be an inward, but comfortable tension exerted against the head of the wearer when buckle 54 is tightened to enable the shield 20 to maintain in the desired position.

Shield 20 is manufactured of a vinyl or other plastic or can even be made of metal of a foraminous nature.

The compression device or pad 32 may be made of known materials, such as thumb, gauze, paper or even an envelope filled with air or liquid, diaphenous-porous solid or gel.

In the normal procedure, the ophthalmic shield 20, together with the pad 32, will be secured or immobilized in place as shown in FIG. 1. After a period of time, such as 24 hours, the shield 20 with the pad 32 can be easily removed by a medical assistant, doctor or patient. Since this is accomplished by loosening or movement of the strap 24 through buckle 54 to enable the medical assistant to have access to the pad 32 which by this time will probably be holding some body fluid that has drained from the eye. Since the pad 32 is not permanently secured to the shield 20, the medical assistant simply removes the pad 32 and wipes clean the surfaces of the shield 20 which can then be replaced on the patient's head as the strap 20 is positioned against the head of the patient.

The presence of the opening 38, as well as satellite openings 40 then allows a significant quantity of light to reach the eye upon which a surgical trauma, injury or disease procedure has been performed. The patient continues to wear a shield 20 until directed by the physician to cease such wearing.

In the event any complications develop, a simple matter to install a new pad 32 which is readily positioned in place as shown in FIG. 2.

Should it be desired to use shield 20 upon the right eye of the patient, it is a simple matter to turn shield 20 so that tab 42 faces to the left, remove special end 52 from small upper opening 44 and replace it in small lower opening 46 by pressing bead 50 in opening 46.

By way of summary, the shield of the present invention is not just for surgery, but also may be used for:

(1) injured eye.
(2) infected eye.
(3) eye that needs protection from external forces.
(4) eye that has to be kept closed.

The pad is for:
(1) adsorption.
(2) lid fixation and in addition to being removable, is also replacable.

The strap may be one piece with a length/tension adjustor.

The shield holes are to maximize viewing:
(1) control.
(2) upward.
(3) downward for walking.

Without further elaboration, the foregoing will so fully illustrate our invention that others may, by applying future knowledge, adopt the same for use under various conditions of service.

What is claimed as the invention is:

1. An ophthalmic shield with compression device comprising an ophthalmic shield having at least one enlarged opening therein, said ophthalmic shield being adapted to be positioned on the head of a human wearer in covering relationship to an eye of the wearer and wherein a fluid absorbent, sanitary compression device passes through and is immobilized in said enlarged opening and extends beyond said enlarged opening, said compression device receiving fluid that drains from said eye and a strap secured to the opthalmic shield.

2. The ophthalmic shield of claim 1 wherein enlarged bead projections extend from the first ends of the strap pieces.

3. The ophthalmic shield of claim 1 having an extension tab extending to one side.

4. The ophthalmic shield of claim 3 wherein said extension tab enables the use of said ophthalmic shield with either the right eye or left eye of a wearer.

5. The ophthalmic shield of claim 1 wherein said strap comprises two-pieces, first ends of which ar secured to the ophthalmic shield, said first ends having bead portions, said strap two-pieces having second ends that are adjustably secured together.

6. The ophthalmic shield of claim 6 wherein said ophthalmic shield further includes a tab extension, first small openings adjacent to the tab extension and a second small opening remote from the tab extension, said strap assembly possessing a bead portion extending from said strap pieces and said bead portion being adapted to be secured in one of said openings.

7. The ophthalmic shield of claim 1 wherein said enlarged opening is circular and located generally centrally.

8. The ophthalmic shield of claim 7, including arcuate slit openings located above and below said central opening.

9. The ophthalmic shield of claim 1, including a sideward extension whereby said shield may be used in connection with either a right eye or a left eye of a human wearer.

* * * * *